(12) United States Patent
Dekel et al.

(10) Patent No.: US 11,844,567 B2
(45) Date of Patent: Dec. 19, 2023

(54) FITTING AND DIRECTING AN EXPANDABLE CATHETER BASED ON AUTOMATIC PULMONARY VEINS ANATOMICAL CHARACTERIZATION

(71) Applicant: Biosense Webster (Israel) Ltd., Yokneam (IL)

(72) Inventors: Zvi Dekel, Zichron Yaakov (IL); Eid Adawi, Tur'an (IL); Fady Massarwi, Baka Al Gharbiyya (IL); Avigdor Rosenberg, Kiryat Tiron (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 259 days.

(21) Appl. No.: 17/127,837

(22) Filed: Dec. 18, 2020

(65) Prior Publication Data
US 2022/0061914 A1  Mar. 3, 2022

Related U.S. Application Data

(60) Provisional application No. 63/071,979, filed on Aug. 28, 2020.

(51) Int. Cl.
*A61B 18/14* (2006.01)
*A61B 18/00* (2006.01)

(52) U.S. Cl.
CPC ............ *A61B 18/1492* (2013.01); *A61B 2018/00214* (2013.01); *A61B 2018/00351* (2013.01); *A61B 2018/00577* (2013.01); *A61B 2018/00982* (2013.01); *A61B 2018/1405* (2013.01)

(58) Field of Classification Search
CPC ...... A61B 18/1492; A61B 2018/00214; A61B 2018/00351; A61B 2018/00577; A61B 2018/00982; A61B 2018/1405; G06T 7/00

See application file for complete search history.

(56) References Cited

U.S. PATENT DOCUMENTS

| 6,514,249 B1 * | 2/2003 | Maguire ............... A61N 7/02 606/41 |
| 8,456,182 B2 | 6/2013 | Bar-Tal et al. |
| 10,096,105 B2 | 10/2018 | Hareland |
| 2009/0182287 A1 * | 7/2009 | Kassab ............... A61B 5/287 606/41 |

(Continued)

FOREIGN PATENT DOCUMENTS

| EP | 2499589 B1 | 11/2016 |
| WO | 2004/034869 A2 | 4/2004 |

(Continued)

OTHER PUBLICATIONS

Extended European Search Report dated Jan. 27, 2022, from EP Application No. 21193358.5, 14 pages.

*Primary Examiner* — Linda C Dvorak
*Assistant Examiner* — Abigail Bock
(74) *Attorney, Agent, or Firm* — Troutman Pepper Hamilton Sanders LLP (57) ABSTRACT

A method includes, using anatomical data, calculating multiple cross-sectional shapes of a lumen of an organ in a body of a patient at multiple respective positions on a medial axis of the lumen. One or more of the positions on the medial axis are identified, at which a given expandable frame of a catheter would fit the cross-sectional shapes. The one or more identified positions are presented to a user.

22 Claims, 4 Drawing Sheets

(56) References Cited

U.S. PATENT DOCUMENTS

| | | | | |
|---|---|---|---|---|
| 2013/0261655 A1* | 10/2013 | Drasler | ............... | A61B 6/485 606/194 |
| 2018/0116723 A1 | 5/2018 | Hettrick et al. | | |
| 2019/0125193 A1 | 5/2019 | Saito et al. | | |
| 2019/0343578 A1 | 11/2019 | Olson | | |
| 2020/0205932 A1* | 7/2020 | Zar | ................ | A61B 5/063 |
| 2020/0265618 A1 | 8/2020 | Chen et al. | | |

FOREIGN PATENT DOCUMENTS

| | | |
|---|---|---|
| WO | 2019/083727 A1 | 5/2019 |
| WO | 2019/209767 A1 | 10/2019 |
| WO | 2020/053831 A1 | 3/2020 |

* cited by examiner

FIG. 6

FITTING AND DIRECTING AN EXPANDABLE CATHETER BASED ON AUTOMATIC PULMONARY VEINS ANATOMICAL CHARACTERIZATION

CROSS-REFERENCE TO RELATED APPLICATIONS

This application claims the benefit of U.S. Provisional Patent Application 63/071,979, filed Aug. 28, 2020, whose disclosure is incorporated herein by reference.

FIELD OF THE INVENTION

The present invention relates generally to medical probes, and particularly to methods of using balloon catheters.

BACKGROUND OF THE INVENTION

Various methods to estimate a cross-sectional geometry of a lumen to facilitate catheter-based treatment were reported in the patent literature. For example, U.S. Patent Application Publication 2009/0182287 describes devices, systems, and methods to identify the locations of intraluminal structures and medical devices during non-surgical medical techniques, such as cardiac ablation, by determining the intraluminal conductance and/or cross-sectional area at a plurality of locations within the body lumen. In an embodiment, as a clinician manipulates a balloon catheter, the manipulation reflects, in relative terms, the lumen's changing electric conductance, and therefore its changing cross-sectional area.

As another example, U.S. Pat. No. 10,096,105 describes a method and system for automatic location of a target treatment structure, such as a pulmonary vein ostium, from an anatomical image. The method includes calculating a most likely path of blood flow through a pulmonary vein based on a cross-sectional area minimization technique and calculating pulmonary vein geometry as a function of length. For example, a pulmonary vein ostium may be located by analyzing a change in pulmonary vein dimensional size or other anatomical factors, such as absolute size. The method may include determining a plurality of centroids along a length of the pulmonary vein. The method may be an algorithm performed by a processing unit of a navigation system or other component of a medical system.

U.S. Patent Application Publication 2019/0343578 describes an electrophysiology catheter that conforms to a shape of a pulmonary vein receiving ablation therapy for a cardiac arrhythmia and produces a consistent tissue ablation line along a length and circumference of the pulmonary venous tissue. During inflation certain portions of the oval cross-sectional shape of the pulmonary vein may be overly stressed, while other portions of the pulmonary vein do not contact the ablation balloon limiting efficacy of the ablation therapy. Accordingly, aspects of the present disclosure are directed to an ablation balloon with a substantially oval shape.

SUMMARY OF THE INVENTION

An embodiment of the present invention that is described hereinafter provides a method including, using anatomical data, calculating multiple cross-sectional shapes of a lumen of an organ in a body of a patient at multiple respective positions on a medial axis of the lumen. One or more of the positions on the medial axis are identified, at which a given expandable frame of a catheter would fit the cross-sectional shapes. The one or more identified positions are presented to a user.

In some embodiments, the one or more identified positions include a contiguous range of positions on the medial axis of the lumen.

In some embodiments, the calculated cross-sectional shapes are orthogonal to the medial axis at the respective positions. In other embodiments, the cross-sectional shapes are oval.

In an embodiment, identifying the positions includes fitting the cross-sectional shapes to respective ellipses, and identifying the one or more positions for which the ellipses have an ovality index larger than a predefined value, wherein the ovality index is defined as maximal for a circle.

In some embodiments, the method further includes, for at least one of the identified positions, presenting to the user an indication indicative of a diameter of the expandable frame of the catheter that would fit a cross-sectional shape of the lumen.

In an embodiment, presenting the identified positions includes marking the one or more identified positions on a medial cross-section diagram of the lumen.

In another embodiment, the lumen is a pulmonary vein (PV), and identifying the positions includes identifying the one or more positions at which the given expandable frame of the catheter would fully occlude the PV.

In some embodiments, the method further includes identifying, at the one or more of the positions, respective directions at which the given expandable frame of a catheter would fit the cross-sectional shapes.

In some embodiments, the lumen is a pulmonary vein (PV), and wherein identifying the respective directions includes identifying respective directions at which the given expandable frame of the catheter would fully occlude the PV.

In an embodiment, the method further includes, using a graphical tool, indicating to the user that the direction of the given expandable frame is angularly aligned, within a pre-specified tolerance, with a tangent to the medial axis of the lumen at the one or more of the positions.

In another embodiment, indicating that the given expandable frame is angularly aligned includes re-coloring a display of electrodes disposed over the expandable frame of the catheter.

There is additionally provided, in accordance with another embodiment of the present invention, a system including a memory and a processor. The memory is configured to store anatomical data of lumen of an organ in a body of a patient. The processor is configured to (a) calculate, based on the anatomical data, multiple cross-sectional shapes of the lumen at multiple respective positions on a medial axis of the lumen, (b) identify one or more of the positions on the medial axis, at which a given expandable frame of a catheter would fit the cross-sectional shapes, and (c) present the one or more identified positions to a user.

The present invention will be more fully understood from the following detailed description of the embodiments thereof, taken together with the drawings in which:

DETAILED DESCRIPTION OF EMBODIMENTS

Overview

Various medical conditions involving a lumen of the body, such as drug-resistant atrial fibrillation (AF), may be treated by an expandable catheter having a general form of an ellipsoidal surface over at least portion of an expandable frame of the catheter, with respect to a longitudinal axis of the catheter.

For example, a lumen can be treated by balloon catheter ablation or expansion, or by another type of expandable catheter for ablation, such as a basket catheter.

In a typical AF balloon ablation procedure, a distal end of a catheter, which is fitted with a balloon comprising ablative elements (e.g., electrodes), is inserted into an ostium of a pulmonary vein (PV) to ablate arrythmogenic tissue of an ostium of the PV. To efficiently and safely isolate the arrythmia, an entire circumference of the ostium should be ablated, preferably simultaneously (i.e., in a "single-shot").

When ablating the PV with a balloon ablation catheter, results show that the success rate of a single-shot ablation are highly correlated with the anatomical characteristics of the PV being treated. For example, narrow PVs, or highly oval PVs, have a lower success rate than larger and rounder PVs, typically due to lower occlusion of the PV by the balloon. To date, the ablation may be optimized mainly based on operator expertise and/or verification of occlusion by an additional modality (such as fluoroscopy).

Embodiments of the present invention that are described hereinafter use a processor to determine preferable positions (e.g., a region) along a medial axis with reference to the average diameter of the lumen (e.g., the curve in FIG. 3 for the PV Average diameter) for placing an expandable catheter, e.g., an inflatable ablation balloon catheter. In some embodiments, the processor further determines preferable directions of the expandable catheter at the preferable respective positions. The embodiments use pre-acquired anatomical data of a lumen, such as an anatomical map of a PV, based on which the processor calculates the medial axis of the PV, and then calculates multiple cross-sectional shapes of the lumen (e.g., PV) at multiple respective positions along the medial axis. In an embodiment, the calculated cross-sectional shapes are orthogonal to the medial axis at the respective positions.

Then, from the cross-sections, the processor identifies (e.g., estimates) one or more positions (e.g., a range of positions) which a given expandable frame of a catheter would fit the cross-sectional shapes. For example, the processor may identify positions that a particular balloon best fit to occlude the lumen. In an embodiment, the one or more identified positions include a contiguous range of positions on the medial axis of the lumen. The processor typically presents the one or more identified positions to a user.

The processor may estimate, for example, cross-sectional ovality of a PV where a balloon having a particular equatorial diameter would best fit. For example, for single-shot ablation, the processor may prefer medial positions at which the lumen ovality is close to a circle, and exclude medial positions high PV cross-sectional ovality.

In some embodiments, the processor calculates an ovality index as a function of a medial axis position, and uses the ovality index to determine the best-suited PV region at which to position a balloon of a given equatorial diameter. For example, in one embodiment the processor determines that PV regions with an ovality index above a certain threshold (with ovality-index defined as maximal for a circular cross-section) are suitable for single-shot balloon ablation. Subsequently, the processor compares the average diameter of the PV at those regions to diameters of available balloons to check if a suitable balloon exists with which a single-shot ablation can be performed. Alternatively, the processor may determine that only segmented (e.g., piecewise) ablation can be performed to ablate an entire circumference of the PV.

In some embodiments, the processor is further configured to, for at least one of the identified positions, present to the user an indication indicative of a diameter of the expandable frame of the catheter that would fit a cross-sectional shape of the lumen. In an embodiment, the processor is configured to present the identified positions by marking the one or more identified positions on a medial cross-section diagram of the lumen.

In one embodiment, the processor colors a map of the PV indicating the best-fit region. In one embodiment, the color for the region is selected according to an ovality index being above a predefined threshold. In another embodiment, a color code is used to reflect the different values of the ovality index along the medial axis. The colored display therefore assists the operator to decide if and where a single-shot balloon-ablation procedure can be performed over a PV medial location.

In yet another embodiment, the processor estimates the quality of fit (e.g., best fit) of a balloon to PV anatomy using an additional criterion to that of the ovality index (e.g., using a metric to determine if the fit is very good, good, fair, or poor). For example, a best-fit method may be used that requires an equatorial diameter of a balloon to give an area equal to the cross-sectional area of the PV, in addition to the PV having a large enough ovality index at the PV position. Using such requirements, the processor may find a best medial axis location that minimizes a difference between the circumference of the PV and the equatorial circumference of the balloon, where such a difference depends on the ovality index, as described below.

In some embodiments, the processor calculates tangents to the medial curve at the preferable positions which are used as preferable directions of the expandable frame of the catheter at the respective positions.

In some embodiments, during an invasive procedure, a position and direction of the expandable frame of the catheter are tracked and the user receives an indication on an anatomical map how accurately the catheter is positioned and directed. To this end, the processor compares a tracked direction of a longitudinal axis of the frame with the tangent to the median at the position, and indicates if the frame is angularly aligned with the tangent within a prespecified angular tolerance.

As the electrodes are typically radially arranged over the frame (e.g., balloon membrane), proper angular alignment of a longitudinal axis of the frame directs the catheter in a direction symmetric with respect to the anatomy, which brings more electrodes into firm contact. In an embodiment, the processor indicates a degree of catheter direction accuracy by graphically showing (e.g., coloring) a progressive number of electrodes of the catheter as being in contact with tissue. When all of the electrodes are colored (e.g., deemed by the angular alignment being within tolerances), the user knows that the catheter is sufficiently well directionally aligned relative to anatomy to perform its functions (e.g., balloon ablation of an ostium of a PV).

Available balloon diameters for PV ablation fall in the range of approximately 15-30 millimeters, and during checking a best fit, the processor identifies a most suitable balloon diameter to select. As noted above, and more rarely, the processor may determine that single-shot balloon ablation of the PV is not possible, as no region of the PV is both circular enough and sized to accommodate a balloon of available diameter. In the latter case, as suggested above, the physician may select a balloon that is suitable for performing segmented ablation (i.e., multiple-shot ablation).

Typically, the processor is programmed in software containing a particular algorithm that enables the processor to conduct each of the processor related steps and functions outlined above.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. Note also that the term "proximal" indicates a location closer to the operator whereas "distal" indicates a location further away to the operator or physician.

While the disclosed embodiments describe elliptically shaped lumen cross-sections, the method may be applied with other lumen cross-sectional shapes (e.g., distorted circle) and with best fitting non-circular balloons (e.g., half spheroid).

By estimating a PV region best suited for positioning a particular balloon, and optionally estimating the best direction of the balloon at the PV region, balloon treatments in general, and balloon ablation procedures in particular, may be made safer and more effective.

System Description

Figure 1:
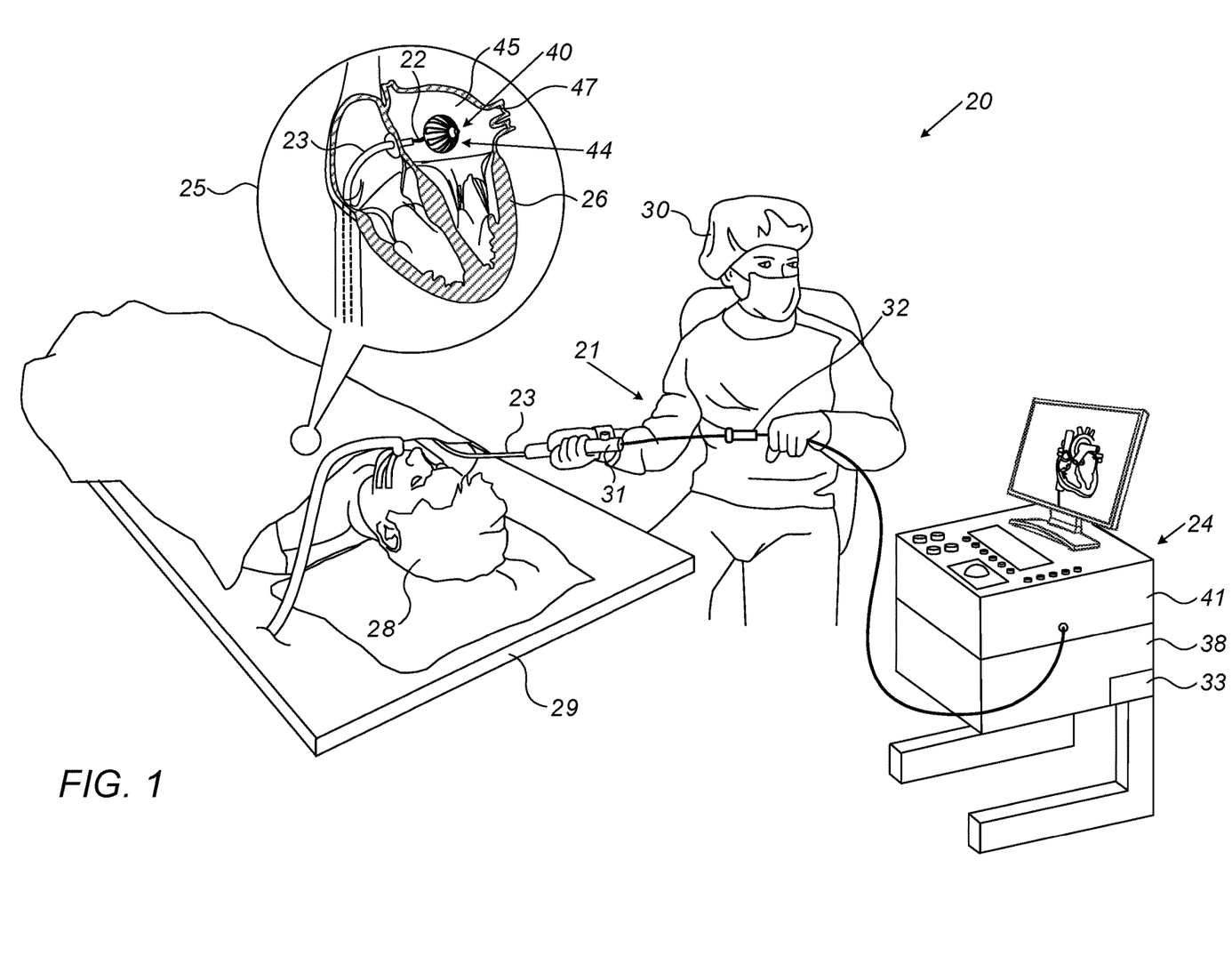
FIG. 1 is a schematic, pictorial illustration of a balloon-catheter based ablation system, in accordance with an embodiment of the present invention.

FIG. 1 is a schematic, pictorial illustration of a balloon-catheter-based ablation system 20, in accordance with an embodiment of the present invention. System 20 comprises a catheter 21, wherein, as seen in inset 25, an ablation balloon 40 fitted at a distal end of shaft 22 of the catheter is inserted, by a physician 30, through a sheath 23 into a left atrium 45 of heart 26 of a patient 28 lying on a table 29.

To reach a target location inside left atrium 45, shown to be an ostium of a pulmonary vein (PV) 47, physician 30 navigates the distal end of shaft 22 by manipulating shaft 22 using a manipulator 32 near the proximal end of the catheter and/or deflection from the sheath 23. Physician 30 then maneuvers balloon 40 inside left atrium 45 using catheter handle 31 so as to access and contact target PV 47 ostium tissue.

To navigate balloon 40, electrical signals from individual electrodes 44 of the balloon can be used with an electrical tracking sub-system and method named Advanced Current Location (ACL), and implemented in various medical applications, for example, in the CARTO™ system, produced by Biosense-Webster Inc. The ACL method enables tracking a position and direction of a frame of a catheter (e.g., direction of a longitudinal axis of a balloon catheter, seen in FIG. 5). The system and method are described in detail in U.S. Pat. No. 8,456,182 whose disclosure is incorporated herein by reference.

As described above, PV 47 ostium may have an odd shaped cross-section (e.g., oval), and it is important to determine a correct medial position along the ostium region to place the balloon, i.e., where the ovality is minimal, in order to achieve uniform single-shot balloon ablation.

The proximal end of catheter 21 is connected to a control console 24, which comprises a processor 41, typically a general-purpose computer. Processor 41 has suitable front end and interface circuits 38 for receiving signals from catheter 21, as well as for applying treatment via catheter 21 in heart 26 and for controlling the other components of system 20. Processor 41 is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, including in FIG. 4, that enables processor 41 to perform the disclosed steps, as further described below.

The example configuration shown in FIG. 1 is chosen purely for the sake of conceptual clarity. The disclosed techniques may similarly be applied using other system components and settings. For example, system 20 may comprise other components and perform non-cardiac treatments.

Figure 2:
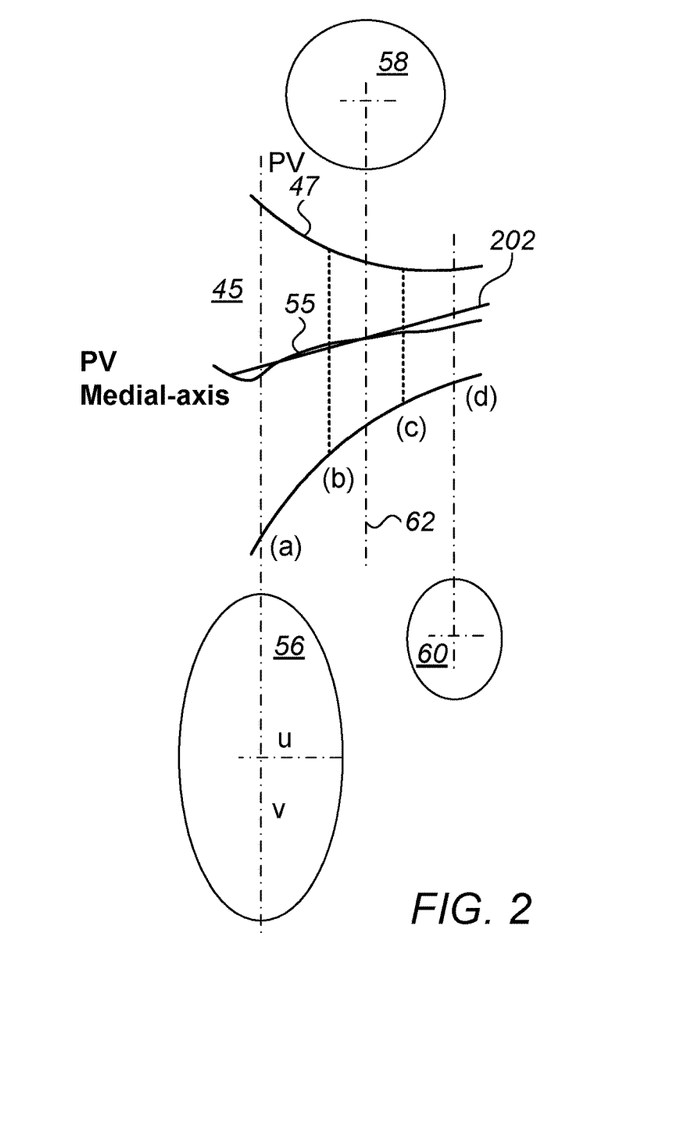
FIG. 2 is a schematic illustration of variable cross-sectional ovality of pulmonary vein (PV) anatomy, in accordance with an embodiment of the present invention.

Ablation Balloon Fitting Based on Automatic Pulmonary Vein Anatomical Characterization FIG. 2 is a schematic illustration of variable cross-sectional ovality of pulmonary vein (PV) 47 anatomy, in accordance with an embodiment of the present invention. As seen, at a medial axis position (a), where left atrium 45 and the ostium of PV 47 approximately join, the shape of cross section 56 of the PV is highly oval, with the oval, by example an ellipse, having a long axis V considerably larger than its short axis U. As further seen, around a medial axis location 62, between medial positions (b) and (c), the shape of cross section 58 of the PV is approximately circular, and at a medial axis positions (d), cross section 60 is again oval. As used herein, "medial axis" is used to indicate one or more centerlines (or center-curves) of the surfaces defining a lumen of an organ, such as, for example, the pulmonary vein into the left atrium. In the present context, the term "medial axis" is also referred to as "centerline" or "medial".

A degree of ovality can be defined in various ways. The description gives hereinafter two useful definitions.

A first ovality index, O–index1, is defined as $$O-index1 = 100\frac{u}{v}; v \geq u$$

As can be seen, a circle (having v=1.25u) has an O–index1=100.

A mildly oval ellipse (e.g., with v=1.25u) has an O–index=80. And a highly oval ellipse (e.g., with v=2u) has an O–index1=50.

Another definition of the ovality index is based on the ratio η, $$\eta = \frac{v-u}{v+u}; v \geq u \qquad \text{Eq. 1}$$

Using η, an ovality index, O–index2, is defined as $$O\text{--index2}=100[1-2\eta], \text{ for } \eta<0.5 \qquad \text{Eq. 2}$$

The two definitions of ovality indices almost coincide (e.g., differ by a small percentage) for O–index values above 80, and are similar for most practical purposes, e.g., not differing by more than 10% for O–index values above 60. Thus, selecting which O–index to use may depend on other considerations, such as a best-fitting method used, as described below using O–index2. However, in case of extreme ovalities (e.g., for v≥3u; η≥0.5) O–index1 should be used.

An additional useful measure of a PV is now defined, being an average diameter of the PV at a given medial position, the average diameter being (v+u). As seen, the average diameter of a circular cross-section PV is the circle diameter of the circular cross-section PV. Using another definition of average diameter, $\sqrt{4uv}$, yields slightly lower average diameters for v≤3u.

As FIG. 3 below shows, given the ovality index and the average diameter of the PV as a function of medial axis position of PV 47, a processor, such as processor 41, can identify the best region on the medial axis for placing an ablation balloon of a given diameter. The processor can also determine that single-shot balloon ablation of PV 47 is infeasible, e.g., if no region of PV 47 is circular enough. Single-shot ablation can also be regarded infeasible if no balloon size is available for any region that is deemed circular enough, since the lumen diameter is too small or too large for a balloon.

Figure 3:
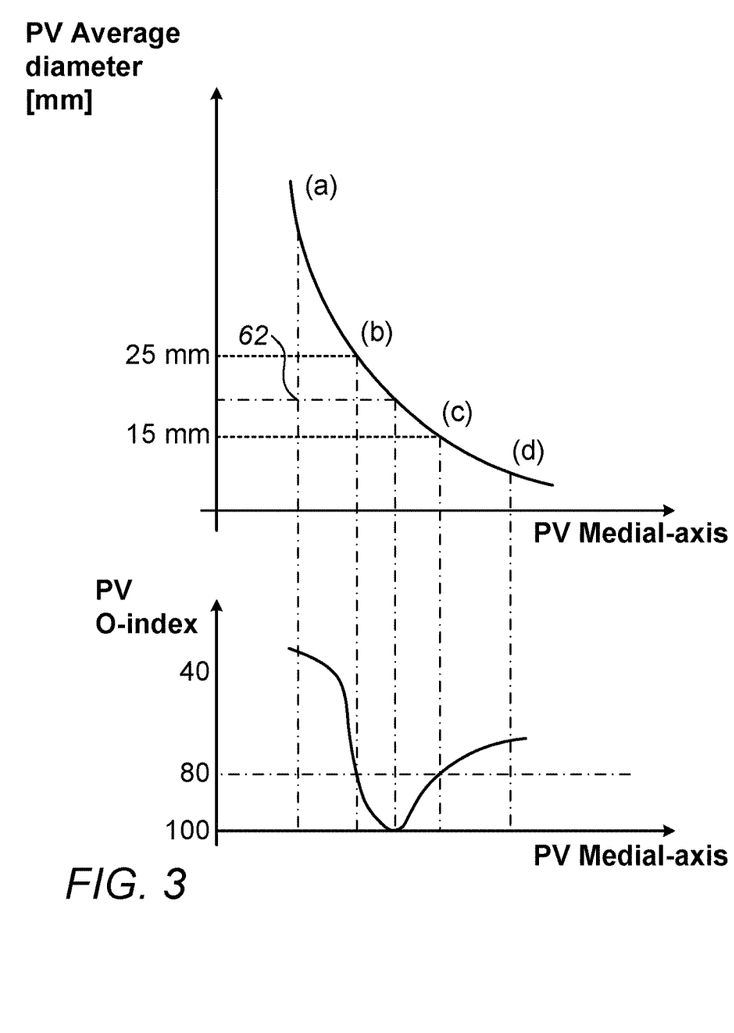
FIG. 3 is a graph of an ovality index and average diameter of the PV of FIG. 2 along the medial axis of the PV, in accordance with an embodiment of the present invention.

FIG. 3 is a graph of an ovality index and average diameter of PV 47 of FIG. 2 along a medial axis 55 of PV 47, in accordance with an embodiment of the present invention. As seen in the bottom graph of FIG. 3, at the medial axis region between medial axis positions (b) and (c) the ovality index (O–index2), called in the graph "PV O–index" of PV 47 (e.g., calculated by processor 41) exceeds a value of 80, which, in one embodiment, is set as a lower threshold for a best-fit criterion, making that region suitable, in principle, for balloon placement.

As top graph of FIG. 3 shows, the calculated average diameter as a function of medial axis position ranges between 15 and 25 millimeters within the ovality index vis-à-vis an eligible region for balloon treatment, i.e., between medial positions (b) and (c).

As balloon diameters between 15 and 25 millimeters are typically available, the physician is notified by the system that such balloons (e.g., a balloon of approximately 20 mm diameter) can be used to perform single-shot ablation of PV 47 at region (b)-(c) of PV 47.

As further seen in FIG. 2, once medial axis location 62 is determined, processor 41 calculates a tangent 202 to the medial curve at the location. In some embodiments, this tangent is used as a target (e.g., suggested) direction of balloon 40, as described in FIG. 5. By extension, the tangents can be calculated for a range of medial positions around medial axis location 62, and each location deemed sufficiently suitable for placing an ablation balloon of a given diameter is also associated with a respective suggested direction for the balloon catheter.

Best Fitting a Balloon Using an
Area-Circumference-Based Metric

As noted above, in another embodiment, the processor estimates a quality of fit of the balloon to an anatomy using a metric on top of ovality index. The additional metric can be more elaborate than the ovality index. For example, using such a metric, the processor can determine if the fit is very good, good, fair, or poor. In an embodiment, a best-fit criterion is provided that requires an equatorial diameter of a balloon to give an area equal to the cross-sectional area of the oval PV.

Using the additional metric, the processor may find a best medial axis location that minimizes a difference between the circumference of the PV and the equatorial circumference of the balloon, where such a difference depends on the ovality index.

To define the above metric, one can write a circumference of an ellipse having an area πuv and a respective η>0 value given (as derived by the mathematician Zafary, 2009) by $$L_E = \pi(v+u)\left(\frac{4}{\pi}\right)^{\eta^2}.$$

Requiring a same balloon cross-sectional area yields, using balloon equatorial diameter, D, D=$\sqrt{4uv}$, an equatorial circumference of the balloon being required to be $$L_B=\pi\sqrt{4uv}.$$

Noting that $L_E > L_B$ always for η>0, one can define a metric as follows, $$F(u,v) = \min_{D_{min}<D<D_{max}} \{(L_E - L_B)\}, \qquad \text{Eq. 3}$$

where a D value that minimizes the positive function (i.e., metric) F(u,v) would be the diameter of the best-fitted balloon. Such a fit may be defined with a tolerance, since PV elasticity may permit less strict fit criteria, such as the actual minimum in Eq. 3.

Combining the requirements over balloon diameters meeting an ovality index (e.g., as defined in Eq. 2) being above a given threshold and at the same time minimizing a metric (as the metric F(u,v) defined in Eq. 3), can provide a flexible tool to determine adequacy and availability of balloon treatment of a given PV.

The above best-fitting method is given by way of example, and other methods may be used, e.g., one that requires a same circumference of PV and equatorial circumference of the balloon, and minimizes differences between respective areas which are covered by embodiments of the present invention.

Selecting an Ablation Balloon for a PV

Figure 4:
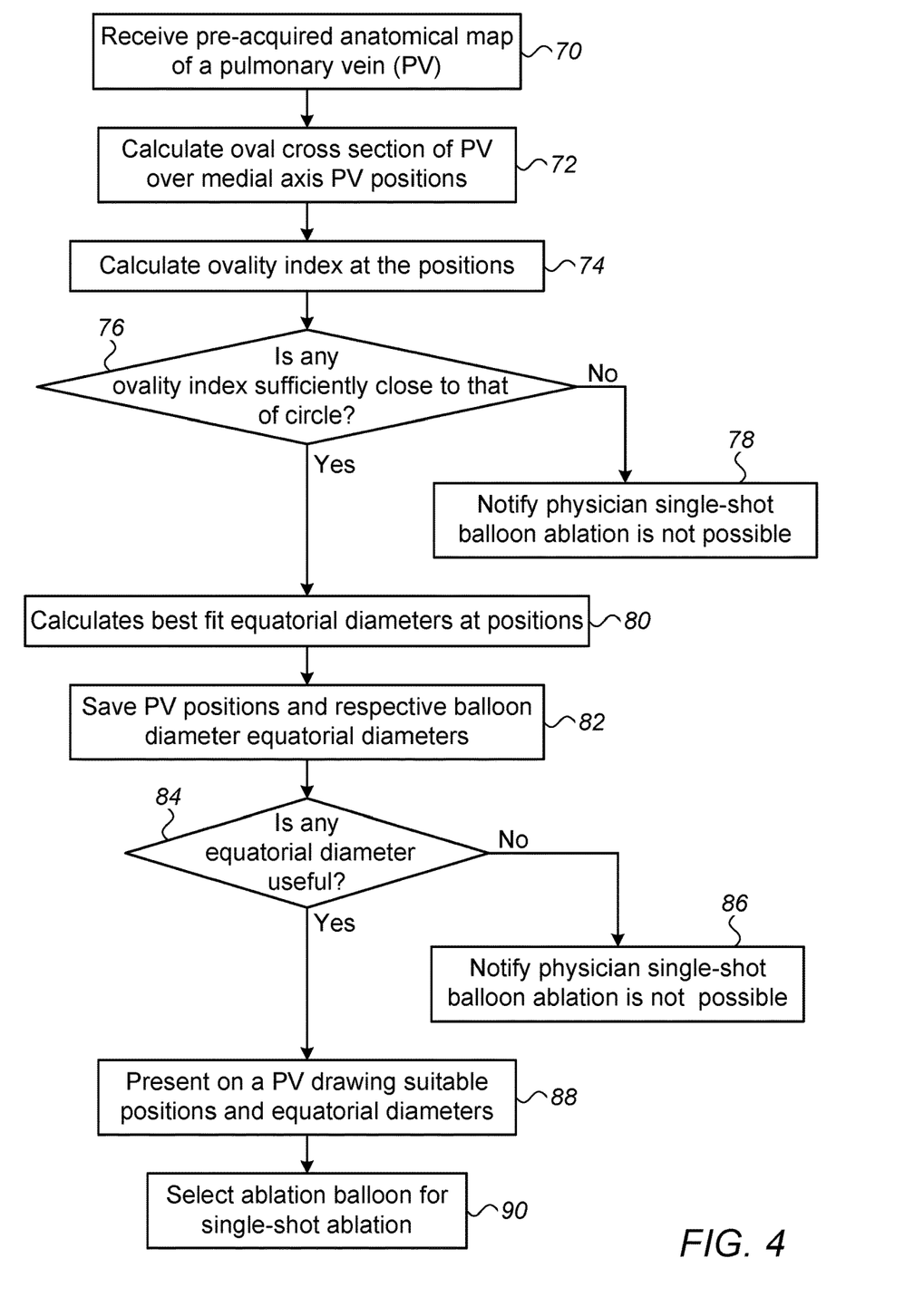
FIG. 4 is a flow chart that schematically illustrates a method for estimating suitability and best position in a pulmonary vein (PV) to perform single-shot balloon ablation, in accordance with an embodiment of the present invention.

FIG. 4 is a flow chart that schematically illustrates a method for estimating suitability and best position in a pulmonary vein (PV) 47 to perform single-shot balloon ablation, in accordance with an embodiment of the present invention. The algorithm, according to the presented embodiment, carries out a process that begins by receiving a pre-acquired anatomical map of PV 47, at a receiving anatomical data step 70. The pre-acquired anatomical map may be uploaded by processor 47 from memory 33 of system 20.

At a cross section calculation step 72, processor 40 calculates an oval cross section of the PV over PV positions on medial axis 55, as described in FIG. 2.

Next, at ovality index calculation 74, processor 40 calculates an ovality index using one of the definitions given above. The ovality index can later be drawn as a function of medial positions as shown in FIG. 3.

At an ovality estimation step 76, processor 40 checks which of the medial positions has an ovality index above a predefined threshold, such that ovality is sufficiently low to be close to that of a zero ovality of a circle.

If no position with sufficiently low ovality is found, processor 40 notifies physician 30 (e.g., on a display of system 20) that a single-shot balloon ablation procedure is not possible for PV 47, at a notification step 78.

At balloon equatorial diameter calculation step 80, processor 40 calculates a best-fit equatorial diameter at the positions found to meet the criterion of step 76. The processor may define a best fit using Eq. 3 or using another best-fit method.

At a logging step 82, processor 40 saves PV positions that meet the criterion of step 76, and the respective best fit balloon equatorial diameters, in memory 33.

At a balloon diameter checking step 84, processor 40 checks which, if any, best-fit equatorial diameters fall in a range of useful (e.g., available) balloon diameters.

If no diameter is found useful, processor 40 notifies physician 30 (e.g., on a display of system 20) that a single-shot balloon ablation procedure is not possible for PV 47, at a notification step 86.

At a presentation step 88, processor 40 presents to physician 30 suitable positions and diameters that meet the criteria of steps 76 and 84, for example using drawings such as those of FIG. 3.

Based on step 88, physician 30 selects an ablation balloon to perform single-shot ablation of PV 47, at an ablation balloon selection step 90.

Figure 5:
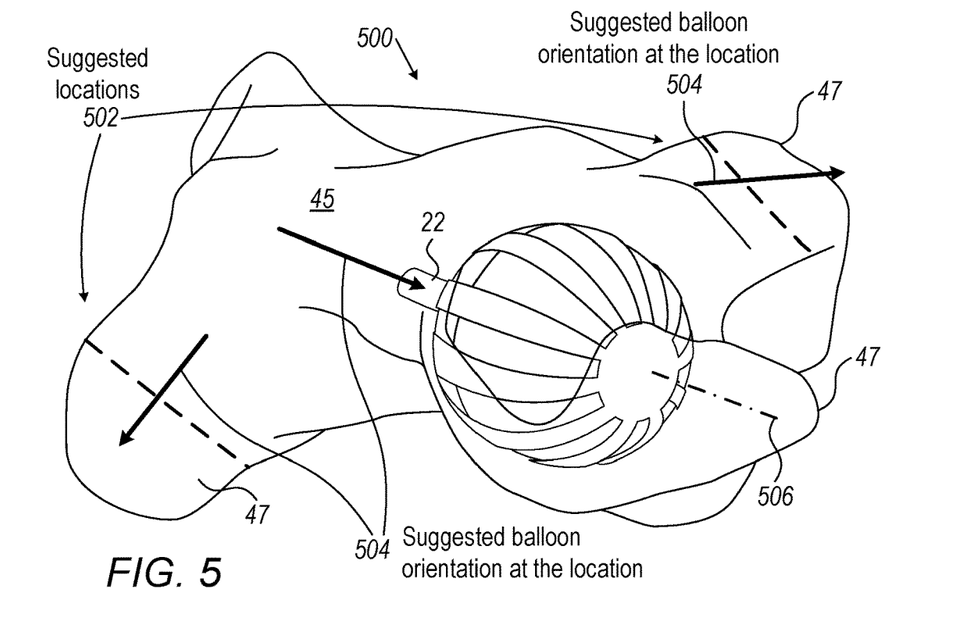
FIG. 5 is schematic, pictorial illustration of a graphical user interface configured to visually indicate a suggested direction of the balloon catheter of FIG. 1 at a suggested PV medial location, in accordance with an embodiment of the present invention.

Suggested Direction of Ablation Balloon Based on Anatomical Characterization FIG. 5 is schematic, pictorial illustration of a graphical user interface configured to visually indicate to a user suggested direction 504 of balloon catheter 40 of FIG. 1 at respectively suggested pulmonary vein (PV) medial location 502, in accordance with an embodiment of the present invention. The graphical user interface is executed by processor 41.

FIG. 5 shows an anatomical map 500 of left atrium 45, with a tracked location and direction of balloon 40 placed inside an ostium of a PV 47. The tracked direction of balloon catheter 40 is given by a longitudinal axis 506 of the catheter, where longitudinal axis 506 is defined as the direction parallel to the distal end of shaft 22.

Two other PV 47 are shown, for which suggested balloon locations 502 (such as position 62 of FIG. 2) and respective directions 504 (such as direction 202 of FIG. 2) are overlaid. During a procedure such as a balloon ablation, the physician may use the tracking system to place the balloon at the suggested locations and respective directions, to ablate the PVs.

In some embodiments, a robotic arm is used for placing the balloon catheter, and a processor commands motion of the arm to bring the catheter into a tracked position and direction that are with a prespecified tolerance relative to a suggested position and direction.

Figure 6:
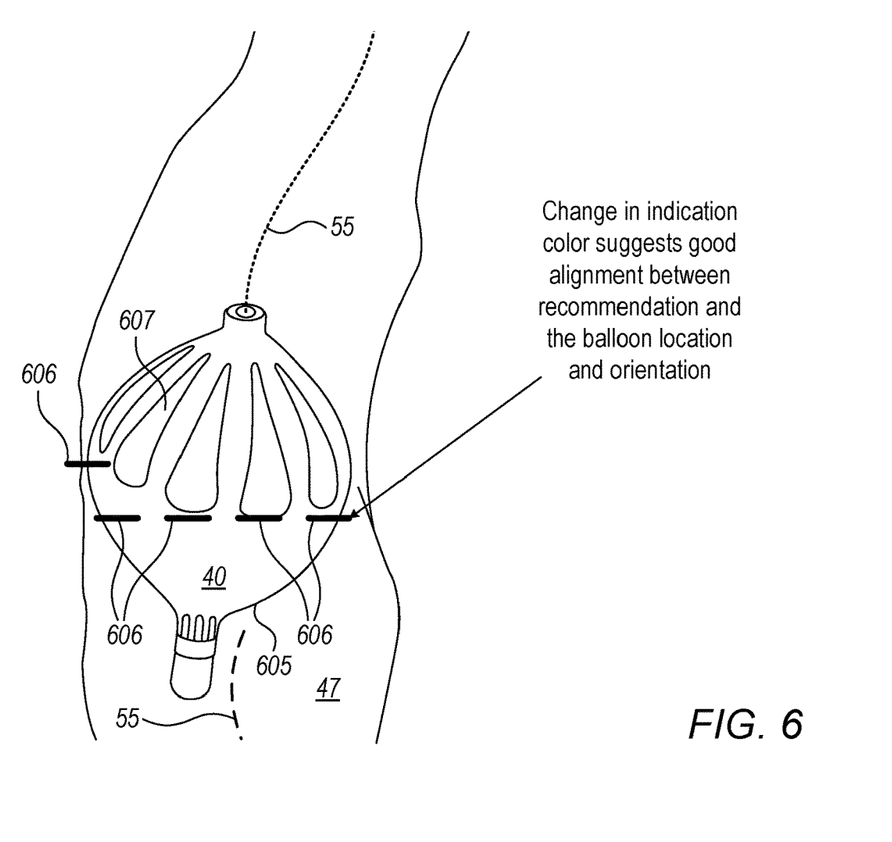
FIG. 6 is schematic, pictorial illustration of a graphical user interface configured to visually indicate a suitable direction of the balloon catheter of FIG. 1 by graphically indicating ready electrodes, in accordance with an embodiment of the present invention.

A graphical application described in FIG. 6 may assist the physician to conclude that the balloon is positioned and directed (manually by the physician or automatically by the robotic arm) as required.

A GUI for Ablation Balloon Best Aligning at Selected Pulmonary Vein Location FIG. 6 is schematic, pictorial illustration of a graphical user interface configured to visually indicate to a user a suitable direction of balloon catheter 40 of FIG. 1 by graphically indicating its ready electrodes 44, in accordance with an embodiment of the present invention. As seen, a map shows balloon 40 placed inside PV 47 having a calculated medial axis 55, and the catheter is visually indicted as being in proper position and direction, as defined above, for example, by changing a color 605 of the balloon (e.g., from blue to green), recoloring (607) electrodes disposed radially over the expandable frame of the catheter and/or underlining (606) a progressively increasing number of electrodes as ready for ablation.

A textual and/or audiovisual indication may be also provided.

Although the embodiments described herein mainly address pulmonary vein isolation, the methods and systems described herein can also be used in other applications, such as in otolaryngology or neurology procedures.

It will thus be appreciated that the embodiments described above are cited by way of example, and that the present invention is not limited to what has been particularly shown and described herein above. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

using anatomical data, calculating multiple cross-sectional shapes of a lumen of an organ in a body of a patient at multiple respective positions on a medial axis of the lumen;

identifying one or more of the positions on the medial axis of the lumen of the organ, at which a given expandable frame of a catheter would fit the cross-sectional shapes;

presenting the one or more identified positions to a user, and indicating, using a graphical tool, that the direction of the given expandable frame is angularly aligned, within a prespecified tolerance, with a tangent to the medial axis of the lumen of the organ at the one or more of the positions.

2. The method according to claim 1, wherein the one or more identified positions comprise a contiguous range of positions on the medial axis of the lumen.

3. The method according to claim 1, wherein the calculated cross-sectional shapes are orthogonal to the medial axis at the respective positions.

4. The method according to claim 1, wherein the cross-sectional shapes are oval.

5. The method according to claim 4, wherein identifying the positions comprises fitting the cross-sectional shapes to respective ellipses, and identifying the one or more positions for which the ellipses have an ovality index larger than a predefined value, wherein the ovality index is defined as maximal for a circle.

6. The method according to claim 1, further comprising, for at least one of the identified positions, presenting to the user an indication indicative of a diameter of the expandable frame of the catheter that would fit a cross-sectional shape of the lumen.

7. The method according to claim 1, wherein presenting the identified positions comprises marking the one or more identified positions on a medial cross-section diagram of the lumen.

8. The method according to claim 1, wherein the lumen is a pulmonary vein (PV), and wherein identifying the positions comprises identifying the one or more positions at which the given expandable frame of the catheter would fully occlude the PV.

9. The method according to claim 1, and comprising identifying, at the one or more of the positions, respective directions at which the given expandable frame of a catheter would fit the cross-sectional shapes.

10. The method according to claim 9, wherein the lumen is a pulmonary vein (PV), and wherein identifying the respective directions comprises identifying respective directions at which the given expandable frame of the catheter would fully occlude the PV.

11. The method according to claim 1, wherein indicating that the given expandable frame is angularly aligned comprises re-coloring a display of electrodes disposed over the expandable frame of the catheter.

12. A system, comprising:

a memory, which is configured to store anatomical data of a lumen of an organ in a body of a patient; and a processor, which is configured to:

calculate, based on the anatomical data, multiple cross-sectional shapes of the lumen of the organ at multiple respective positions on a medial axis of the lumen of the organ;

identify one or more of the positions on the medial axis of the lumen of the organ, at which a given expandable frame of a catheter would fit the cross-sectional shapes;

present the one or more identified positions to a user, and indicate to the user, using a graphical tool, that the direction of the given expandable frame is angularly aligned, within a prespecified tolerance, with a tangent to the medial axis of the lumen of the organ at the one or more of the positions.

13. The system according to claim 12, wherein the one or more estimated positions comprise a contiguous range of positions on the medial axis of the lumen of the organ.

14. The system according to claim 12, wherein the calculated cross-sectional shapes are orthogonal to the medial axis at the respective positions.

15. The system according to claim 12, wherein the cross-sectional shapes are oval.

16. The system according to claim 15, wherein the processor is configured to fit the cross-sectional shapes to respective ellipses, and identify the one or more positions for which the ellipses have an ovality index larger than a predefined value, wherein the ovality index is defined as maximal for a circle.

17. The system according to claim 12, wherein the processor is further configured to, for at least one of the identified positions, present to the user an indication indicative of a diameter of the expandable frame of a catheter that would fit a cross-sectional shape of the lumen of the organ.

18. The system according to claim 12, wherein the processor is configured to present the identified positions by marking the one or more identified positions on a medial cross-section diagram of the lumen of the organ.

19. The system according to claim 12, wherein the lumen of the organ is a pulmonary vein (PV), and wherein the processor is configured to identify the positions by identifying the one or more positions along the medial axis at which the given expandable frame of a catheter would fully occlude the PV.

20. The system according to claim 12, wherein the processor is further configured to identify, at the one or more of the positions along the medial axis, respective directions at which the given expandable frame of a catheter would fit the cross-sectional shapes.

21. The system according to claim 20, wherein the lumen of the organ is a pulmonary vein (PV), and wherein the processor is configured to identify the respective directions by identifying respective directions at which the given expandable frame of the catheter would fully occlude the PV.

22. The system according to claim 12, wherein the processor is configured to indicate to the user that the given expandable frame is angularly aligned by re-coloring a display of electrodes disposed radially over the expandable frame of the catheter.

* * * * *